(12) United States Patent
Bodenschatz

(10) Patent No.: US 7,314,458 B2
(45) Date of Patent: Jan. 1, 2008

(54) ADJUSTABLE SPLINT

(75) Inventor: Stefan Bodenschatz, Buxtehude (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 11/346,254

(22) Filed: Feb. 3, 2006

(65) Prior Publication Data
US 2006/0173391 A1     Aug. 3, 2006

(30) Foreign Application Priority Data
Feb. 3, 2005   (DE)   .................... 10 2005 004 838

(51) Int. Cl.
  *A61F 5/00*   (2006.01)
  *A61F 5/37*   (2006.01)
  *A61G 15/00*  (2006.01)
  *A41D 13/08*  (2006.01)

(52) U.S. Cl. ................ 602/12; 602/19; 602/32; 602/5; 602/6; 602/16; 602/21; 128/845; 128/846; 2/16; 2/910; 2/917

(58) Field of Classification Search ............ 602/19, 602/12, 32; 128/845, 846
See application file for complete search history.

(56) References Cited
U.S. PATENT DOCUMENTS

| 4,522,199 | A | 6/1985 | Waddell et al. | |
| 4,548,199 | A * | 10/1985 | Agee | 606/57 |
| 4,573,455 | A | 3/1986 | Hoy | |
| 5,840,051 | A | 11/1998 | Towsley | |
| 5,848,983 | A | 12/1998 | Basaj et al. | |
| 6,561,994 | B1 | 5/2003 | Mills et al. | |
| 6,565,563 | B1 * | 5/2003 | Agee et al. | 606/55 |
| 6,773,411 | B1 | 8/2004 | Alvarez | |
| 6,997,892 | B2 * | 2/2006 | Reinecke | 602/32 |

FOREIGN PATENT DOCUMENTS

| DE | 3020083 | 3/1981 |
| DE | 422222601 | 1/1994 |
| WO | 01/37718 | 5/2001 |

\* cited by examiner

*Primary Examiner*—Patricia Bianco
*Assistant Examiner*—Tarla Patel
(74) *Attorney, Agent, or Firm*—Greenblum & Bernstein, P.L.C.

(57) ABSTRACT

Splint for an orthopedic joint bandage. The splint includes at least a first section, at least a second section, at least one tensioning element, and a tightening device. The tightening device is structured and arranged to press the first and second sections against each other. This abstract is neither intended to define the invention disclosed in this specification nor intended to limit the scope of the invention in any way.

12 Claims, 4 Drawing Sheets

ADJUSTABLE SPLINT

CROSS-REFERENCE TO RELATED APPLICATIONS

The present application claims priority under 35 U.S.C. §119 of German Patent Application No. 10 2005 004 838.2, filed on Feb. 3, 2005, the disclosure of which is expressly incorporated by reference herein in its entirety.

BACKGROUND OF THE INVENTION

1. Field of the Invention

The invention relates to a splint with adjustable flexural rigidity for orthopedic joint bandages.

2. Discussion of Background Information

Depending on their design and on the indications for which they are intended, orthopedic joint bandages exert a fixing, guiding, bracing and/or supporting action on the joints of the human body. The joint bandages are usually made from flexible shaped articles, for example woven fabrics, knitted fabrics or lined neoprene. The shaped articles have an anatomical shape in order to correspond to the anatomical circumstances and in order to be able to act on the human body with a form fit and force fit. For deliberate stiffening of the joint bandages, one or more stiffening elements, namely splints or rods, are often worked into the joint bandages. These stiffening elements, referred to below as splints, are usually made of metal or plastic.

The stabilizing action of the joint bandages thus depends on the design of the joint bandages and on the number, arrangement and configuration of the splints. A disadvantage is that the stabilizing action chosen by the manufacturer of the joint bandage cannot be individually adjusted by the user. A typical example of such joint bandages is disclosed in U.S. Pat. No. 6,561,994, in which wrist bandages with a nonflexible splint are described. Particularly in wrist bandages, however, an adjustability of the stabilizing action is desirable, for example in order to be able to adapt the bandage to the healing process or to the particular physical activity.

Joint bandages are known in which the user is able to reduce the stabilizing action by removing one or more splints and is able to increase the stabilizing action by reinserting them. It is also known for splints with high flexural rigidity to be replaced, if so required, by splints having less flexural rigidity. For example, U.S. Pat. No. 6,773,411 describes a bandage with exchangeable splints. However, this is very unwieldy, and the stabilizing action can be adjusted in coarse steps, but not individually.

SUMMARY OF THE INVENTION

The invention makes available a splint for orthopedic joint bandages, in which the flexural rigidity of the splint, and thus the stabilizing action of the bandage, can be adapted individually to the needs of the user.

The invention thus relates to a splint as set forth herein and advantageous refinements of the splint, its use, and bandages comprising splints of this kind.

Accordingly, the splint is composed of at least two individual splint sections which are held together by one or more tensioning elements and are pressed against one another by way of a tightening device, via the tensioning elements. The flexural rigidity of the splint made up of the individual sections varies depending on the tensile stress of the tensioning element or tensioning elements.

The splint according to the invention functions in accordance with the following principle of action: The splint sections are arranged displaceably in relation to the tensioning elements and/or the tensioning elements are bendable. When the splint is bent, as is possible through the normal stressing of the bandage, an angular gap appears between two, more or all of the splint sections, with the result that the overall length of the splint is slightly extended. The bending of the splint is thus possible only counter to the adjustable tensile stress of the tensioning elements.

The flexural rigidity of the splint thus depends not only on the adjustable tensile stress but on the design-related elasticity or bending strength of the tensioning elements and on the design-related elasticity or bending strength of the sections. A joint bandage comprising a splint according to the invention thus makes it possible that the bandaged joint is limited in its mobility depending on the chosen tensile stress. The tightening device is advantageously configured such that the tensile stress can also be adjusted and changed with the bandage applied.

It is likewise possible, in the unloaded state of the splint, to adjust a clearance between tensioning elements and splint sections, i.e. the tensioning elements are longer than the splint sections held together by them. A joint bandage comprising a splint of this kind according to the invention thus makes it possible that the bandaged joint remains able to move up to a predetermined angle, but it ensures that mobility beyond this angle is limited or prevented.

According to the invention, the splint is provided with a tightening device with which the level of the tensile stress of the tensioning element or tensioning elements can be quickly and easily adjusted by the user and, if so desired, the clearance between the splint sections can be individually adjusted. To adjust the tensile stress of the tensioning element or tensioning elements, various tightening devices familiar to the skilled person can be chosen for adjusting the tensile stress, for example turnbuckles or set screws. The flexural rigidity of the splint according to the invention, made up of the individual splint sections, varies depending on the tensile stress of the tensioning element or tensioning elements. The tensile stress can in this case be adjusted steplessly or in predetermined steps, depending on the chosen tightening device.

When a higher tensile stress is chosen, with resulting higher flexural rigidity of the splint, the splint will provide an increased resistance upon bending. Greater forces are needed in order to bend the splint. There is therefore a greater stabilizing of the joint. When a low tensile stress is chosen, the splint can be bent with only slight force being applied, the stabilizing of the joint is low and the mobility is retained. Since the tensile stress is adjustable, the stabilizing action of the splint and therefore of the joint bandage can be adapted individually to the medical requirements and to the activity of the user.

In order to avoid mechanical damage in the event of excessive stressing, that is to say in the event of excessive bending of the splint, one or more spring elements can be integrated in the splint. The spring elements can be integrated in the tensioning element(s), between or in the sections, or preferably in the tightening device. However, depending on the choice of material and the design, the elasticity of the tensioning element(s) and/or of the sections may also be sufficient to prevent damage in the event of excessive stressing. Helical springs, for example, can be used as the spring element, but it is also possible for one or all of the sections of the splint to be made at least partially from a rubber-elastic material.

The individual sections of the splint can be of uniform configuration, in order to obtain a uniform adjustable flexural rigidity along the entire length of the splint. However, it is advantageous to adapt the shape of the sections to the particular area of application of the splint.

The areas of mutual contact between the individual sections are advantageously made flat and preferably oriented at a right angle to the longitudinal axis, i.e. in the direction of the tensioning elements. For curved splints, however, it is possible to deviate from the right angle.

In an advantageous embodiment, the tensioning element or tensioning elements provide(s) for the guiding of the sections and prevent(s) lateral shifting of the sections. The tensioning element or tensioning elements are accordingly made flexurally rigid (so as to not be stretched significantly longitudinally), so that they guarantee the lateral guiding. It is advantageous if the tensioning element or tensioning elements extend(s) through the sections.

It is likewise possible, according to the invention, for the contact surface of the sections to be curved, asymmetrically configured or contoured. It is advantageous to provide projections which engage in depressions on the opposing face of the adjoining section and thus prevent lateral shifting of the sections in relation to one another.

The individual sections of the splint can be made from customary materials. It is advantageous to use plastic in order to keep the weight of the splint to a minimum. The tensioning elements can be made from flexible rods with tensile strength, for example rods made of plastic, although it is also possible to use wires or wire lines.

It is likewise possible, by virtue of the design of the sections of the splint according to the invention, to achieve a flexural rigidity that differs depending on the direction of the load. If the contact surface of the sections is a rectangle, then a differing flexural rigidity is obtained depending on the length of the side. With a given tensile stress, a lower flexural rigidity of the splint is obtained upon bending in the direction of the short side of the rectangle than is obtained upon bending in the direction of the longer side of the rectangle. This is very advantageous for use of the splint according to the invention in joint bandages. The supporting action for extension and flexion of the joint can be adjusted by means of the tensile stress. A high level of lateral supporting action is ensured since the splint provides a greater resistance to the lateral bending, that is to say in the direction of the longer side of the rectangle.

In another embodiment, the contact area between the individual sections is curved, such that a linear contact surface is obtained between the sections. The splint thus formed has a very much lower flexural rigidity upon bending transversely with respect to the linear contact surface than it does upon bending in the direction of the linear contact surface.

It is likewise possible for the curvature of the contact surface to be configured asymmetrically with respect to the linear contact surface. This is very advantageous when the splint according to the invention is used in joint bandages. The supporting action for extension and flexion of the joint can be adjusted by means of the tensile stress. By means of the asymmetric configuration of the contact surface, the supporting action for extension and flexion differs greatly.

In addition to the configuration of the contact surface between the sections, it is likewise possible, within the sections, to use materials of different stiffness in order to obtain an adjustable flexural rigidity that is dependent on the direction of loading.

Particularly advantageous embodiments of the splint according to the invention are described below with reference to a number of figures. The splint shown can be fitted as usual to the palmar side of a wrist bandage, for example by pushing it into a pocket provided for this purpose.

The invention also provides for a splint for an orthopedic joint bandage, comprising at least a first section, at least a second section, at least one tensioning element, and a tightening device. The tightening device is structured and arranged to press the first and second sections against each other.

The splint may further comprise at least one spring element arranged at least one of between the first and second sections, within one of the first and second sections, between the tightening device and one of the first and second sections, within the tightening device, and to bias one portion of the tightening device away from another portion of the tightening device.

The first and second sections may be at least one of movably disposed on and movably arranged on the at least one tensioning element. The first and second sections may comprise engaging contact surfaces which are at least one of generally flat and generally rectangular. The first and second sections may comprise engaging contact surfaces which are at least one of generally curved, generally asymmetrical, generally contoured, and generally structured and arranged to engage with one another. The tightening device may be structured and arranged to adjust a tensile stress of the at least one tensioning element. The tightening device may be structured and arranged to smoothly adjust a tension of the at least one tensioning element.

The invention also provides for an orthopedic joint bandage which comprises the splint of the type described above.

The invention also provides for an orthopedic wrist bandage comprising at least one splint of the type described herein.

The invention also provides for an orthopedic wrist bandage which comprises at least one splint as described herein, wherein a supporting action of the bandage can be adjusted for extension, flexion, abduction and adduction when the bandage is applied to a user's wrist.

The invention also provides for a method of adjusting the splint of the type described herein wherein the method comprises arranging and/or removably mounting an orthopedic wrist bandage having the splint of the type described herein on a user's wrist and adjusting a flexural rigidity of the orthopedic wrist bandage.

The invention also provides for a splint for an orthopedic joint bandage comprising a first section, a second section, a tension adjustment device, and at least one tensioning element having one end coupled to the first section and another end coupled to a portion of the tension adjustment device. The second section is arranged between the first section and the tension adjustment device and is movably mounted to the at least one tightening device.

The second section may comprise at least one of a plurality of sections, a plurality of sections each having at least one through opening sized to receive therein the at least one tensioning element, a plurality of substantially similar sections, a plurality of generally rectangular sections having generally flat opposite engaging surfaces, a through opening which receives therein the at least one tensioning element, opposite surfaces which are arranged generally parallel to each other, opposite surfaces which are generally rectangular, and a plurality of sections which have a different configuration than the first section.

The first section may have a partially curved portion which is generally adapted to a shape of a user's palm. The at least one tensioning element may comprise two tensioning elements arranged generally parallel to each other. The first section may comprise engaging contact surfaces which are at least one of partially curved, generally asymmetrical, generally contoured, and generally structured and arranged to engage with one another. The tension adjustment device may be structured and arranged to adjust a tensile stress of the at least one tensioning element. The tension adjustment device may comprise an engaging section which is movably mounted to the at least one tensioning element, an adjusting section which constitutes the portion of the tension adjustment device, and an adjusting member which moves the engaging section away from the adjusting section.

The invention also provides for a splint for an orthopedic joint bandage which comprises a first section, a tension adjustment device, a plurality of second sections arranged between the first section and tension adjustment device, two tension members each having one end secured to the first section and another end secured to a portion of the tension adjustment device, and each second section being movably mounted to the two tension members.

The tension adjustment device may comprise an engaging section which is movably mounted to the two tension members, an adjusting section which constitutes the portion of the tension adjustment device, and an adjusting member rotatably mounted to the adjusting section and configured to move the engaging section away from the adjusting section.

BRIEF DESCRIPTION OF THE DRAWINGS

The present invention is further described in the detailed description which follows, in reference to the noted plurality of drawings by way of non-limiting exemplary embodiments of the present invention, in which like reference numerals represent similar parts throughout the several views of the drawings, and wherein.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
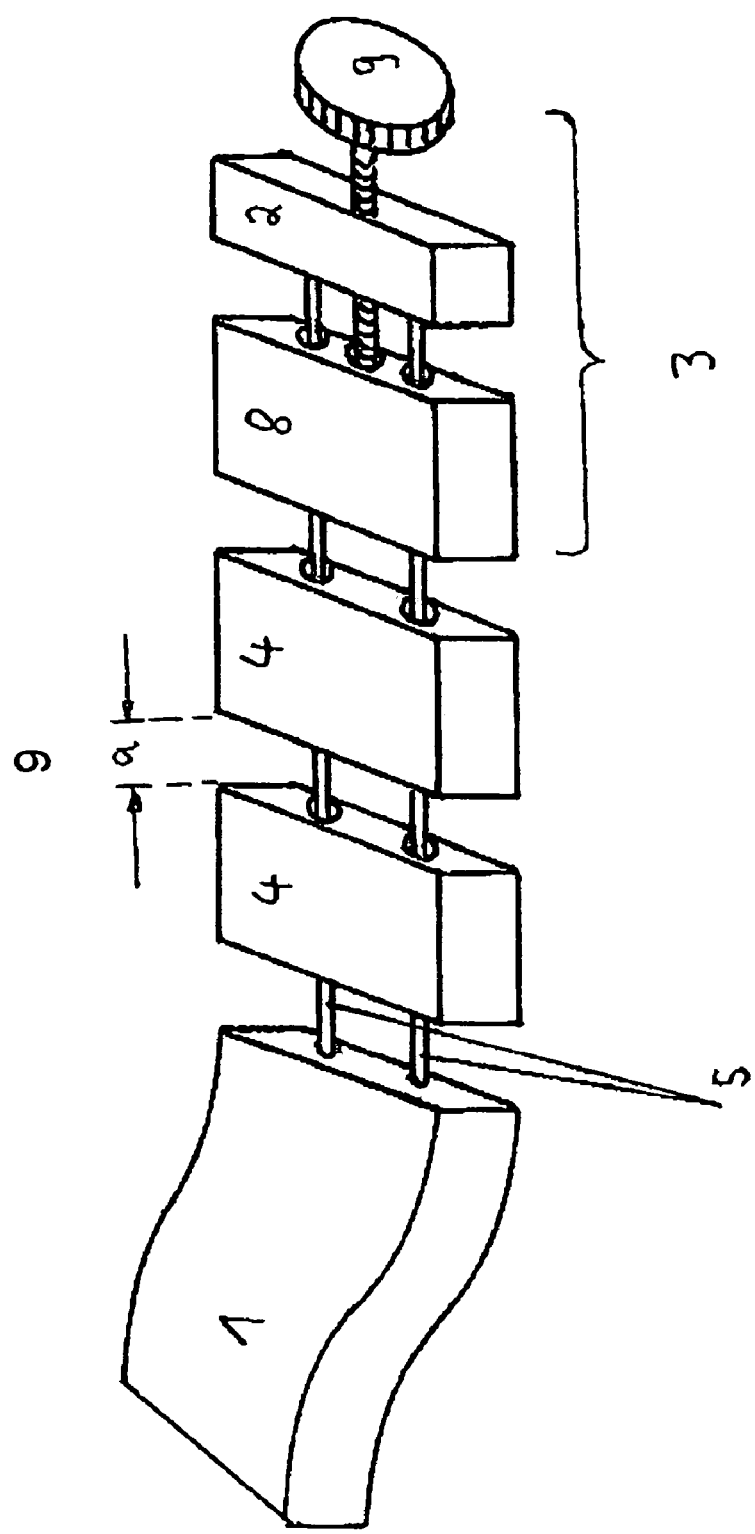
FIG. 1 shows one non-limiting embodiment of the invention.

With reference to FIG. 1, there is shown a particularly advantageous embodiment of the splint according to the invention wherein the tensioning elements are positioned so as not to experience any tensile stress. For improved clarity of the drawing, the tensioning elements are shown lengthened.

The splint has a first section 1 that is adapted to the anatomy of the palmar surface. A plurality of tensioning elements 5, e.g., two or more, are fixedly connected to the first section 1. A number of middle sections 4 are movably disposed and/or mounted on the tensioning elements 5. The tensioning elements 5 run and/or extend through the sections 4 via through openings in the sections 4. The tensioning elements 5 provide for the lateral guiding of the sections 4. The splint also utilizes sections 2 and 8. A knurled-head screw 9 together with the sections 2 and 8 form a simple device 3 for adjusting the tensile stress of the splint and/or form a tightening device 3. The tensioning elements 5 have opposite ends which are fixedly connected to sections 1 and 2. The knurled-head screw 9 has external threads which engage with internal threads situated in section 2. The free end of the screw 9 bears on and/or engages with section 8, and in particular within a recess formed in section 8. As with sections 4, section 8 is movably arranged on the tensioning elements 5 and includes through openings which each receive one of the tensioning elements 5.

The splint thus functions as follows: when the knurled-head screw 9 is unscrewed, e.g., rotated counterclockwise, the space between sections 2 and 8 is increased, and section 1 is accordingly pulled nearer to and in the direction of section 2. In this way, the distance "a" between the displaceably arranged sections 4, between the sections 4 and 1, and between sections 4 and 8 decrease. A tensile stress is thus built up or created in the tensioning elements 5.

According to one non-limiting embodiment of the invention, the tensioning elements 5 have a defined and fixed elasticity. The sections 1, 4 and 8 are made of a specific material and have surface quality. Furthermore, the level of the tensile stress which is thus set determines the flexural strength of the splint. As a result, the supporting action of the wrist bandage which is provided with the splint according to the invention can thus be adjusted for extension and flexion of the joint by way of the tightening device 3.

Figure 2:
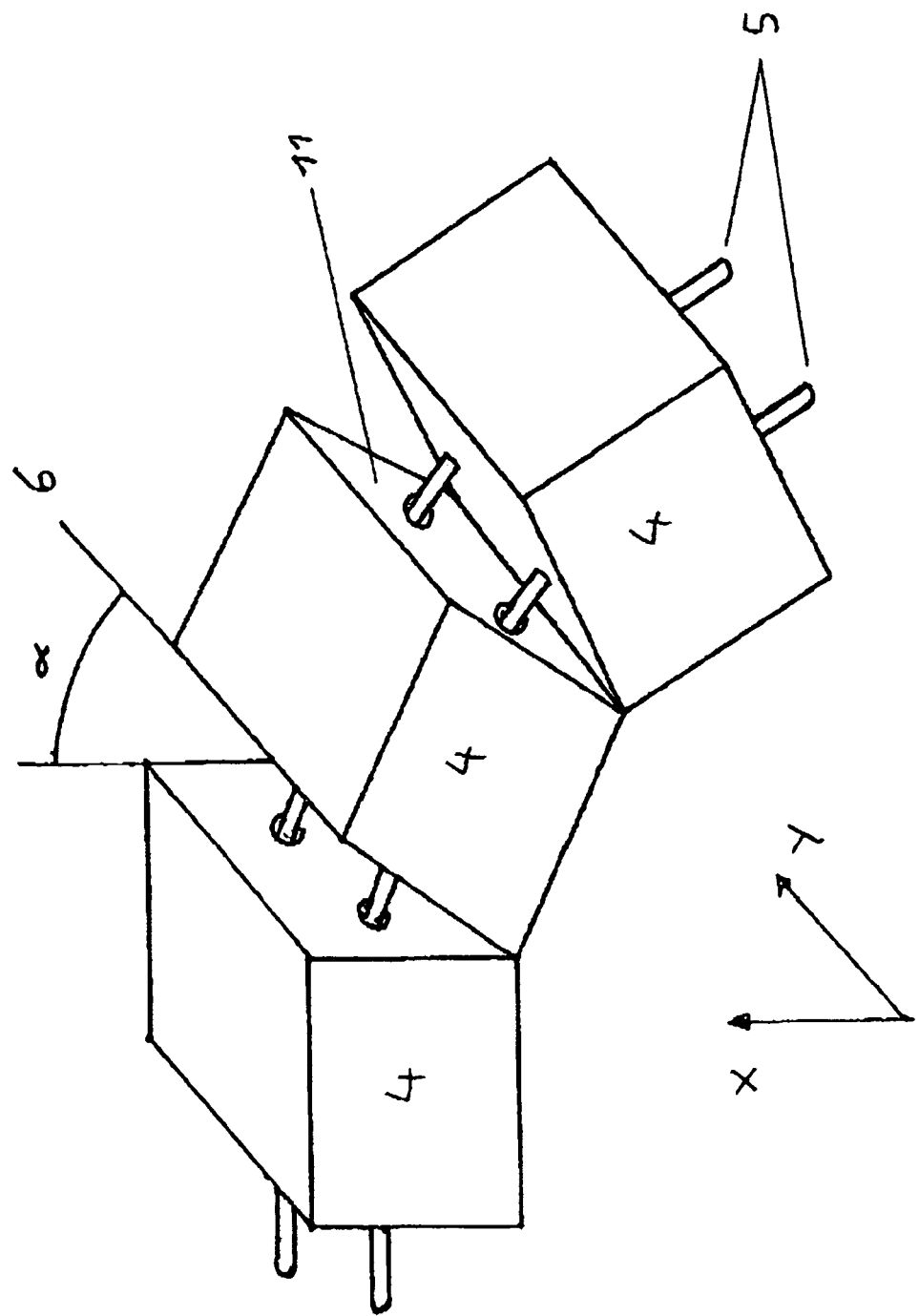
FIG. 2 shows a partial view of another non-limiting embodiment of the invention.

FIG. 2 shows a detail of an advantageous embodiment of the splint according to the invention utilizing three sections 4. This figure provides a clearer understanding of how the mechanism functions. The sections 4 are assumed to be rigid, that is to say they do not deform in the event of loading. When the sections 4 are buckled relative to one another against the tensile stress in the tensioning elements 5, as happens upon bending of the splint, an angular gap 6 results between the sections 4 and this gap has angle "α". This is only possible counter to the adjustable tensile stress of the tensioning elements 5. The mutual buckling of the sections 4, and therefore the flexural rigidity of the splint, thus depends on the elasticity of the tensioning elements 5 and of the sections 4 at a predetermined tensile stress. In this advantageous embodiment, the contact surfaces 11 of the sections 4 are rectangular, so that, upon bending in direction "x", the flexural rigidity of the splint is less than in the case when the splint is bend in direction "y" (direction "y" being generally parallel to surface 11 and perpendicular to direction "x").

Figure 3:
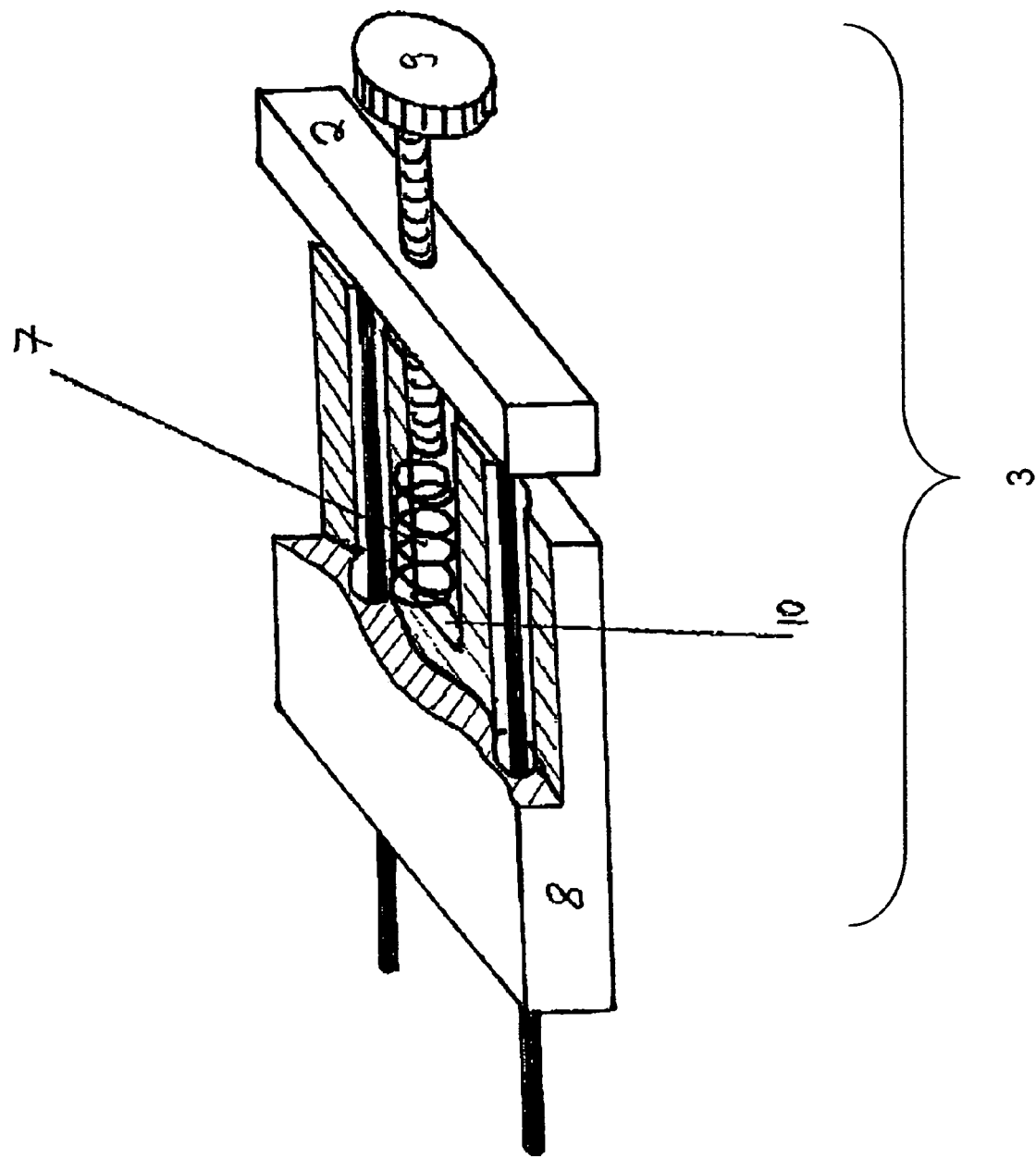
FIG. 3 shows a partial cross-section view the tightening device which can be used on the splint embodiments disclosed herein.

FIG. 3 shows another non-limiting embodiment of the tightening device 3. In this embodiment, the tightening device 3 includes a spring element 7, e.g., a helical compression spring, that can be integrated and/or arranged within in the tightening device 3 and more particularly in section 8. The advantage of the spring 7 is that, in the event of excessive stressing, that is to say excessive bending of the splint, mechanical damage of the splint sections and/or tensioning elements can be avoided because the spring 7 will allow for additional movement of the sections 4 and 8 relative to the tensioning elements 5. In this embodiment of the tightening device 3, the knurled-head screw 9 bears on and/or engages with one end of the helical spring 7. The spring 7 is arranged and/or fitted within a blind hole 10 in section 8 which is sized to allow the spring 7 to extend and compress based on the position of the screw 9.

Figure 4:
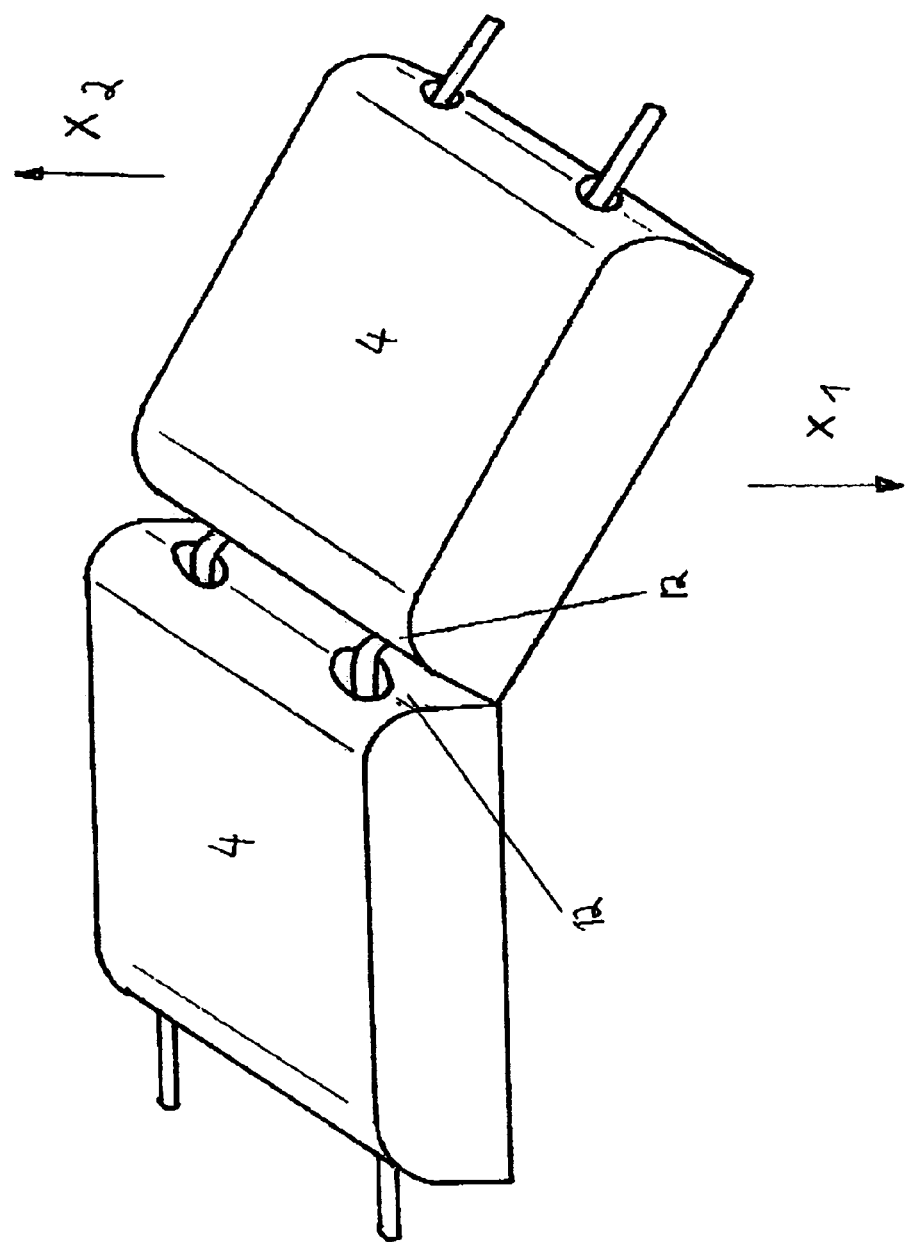
FIG. 4 shows a partial view of another embodiment of the invention.

FIG. 4 shows a detail of an advantageous embodiment of the splint according to the invention wherein sections 4 have a contact surface or corner 12 which is curved and/or has an asymmetrical configuration. As a result of this section 4 configuration, when a bending load is applied in direction X1, a greater flexural rigidity of the splint is obtained than when a load is applied in direction X2.

The splint of the invention can be used on a wrist brace of the type desired by the user. By way of non-limiting example, the splint of the invention can be used on a wrist brace of the type described in U.S. Pat. No. 6,561,994, the disclosure of which is hereby expressly incorporated by reference in its entirety.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

List of the reference numbers used in the Figures:
1 section of the splint, adapted to the anatomy
2 section, component part of the tightening device (3)
3 tightening device for adjusting the tensile stress (e.g. knurled-head screw), if appropriate made up of sections (8), (2) and (9)
4 sections of the splint
5 tensioning elements
6 angular gap α
7 spring element
8 section, component part of the tightening device (3)
9 distance a between the sections (4, 1, 8)
10 blind hole
11 contact surface of the sections (4, 8, 1)
12 curved contact surface of the sections (4)

What is claimed:

1. A splint for an orthopedic joint bandage, comprising:
a first section;
a second section comprising at least one through opening;
a tension adjustment device; and
at least one flexible tensioning element passing through the at least one opening and having one end coupled to the first section and another end coupled to a portion of the tension adjustment device,
wherein the second section is arranged between the first section and the tension adjustment device and is movably mounted to the at least one tensioning element.

2. The splint of claim 1, wherein the second section comprises at least one of:
a plurality of sections;
a plurality of elastically compressible sections;
a plurality of synthetic resin sections;
a plurality of sections having substantially a same thickness;
a plurality of elastically deformable sections;
a plurality of sections each having at least one through opening sized to receive therein the at least one tensioning element;
a plurality of substantially similar sections;
a plurality of generally rectangular sections having generally flat opposite engaging surfaces;
opposite surfaces which are arranged generally parallel to each other;
opposite surfaces which are generally rectangular; and
a plurality of sections which have a different configuration than the first section.

3. The splint of claim 1, wherein the first section has a partially curved portion which is generally adapted to a shape of a portion of a user's palm.

4. The splint of claim 1, wherein the at least one tensioning element comprises at least one of:
two tensioning elements having a smooth outer surface which slides freely within openings in the second section;
two non-longitudinally stretchable tensioning elements;
two generally similarly sized and shaped tensioning elements;
two tensioning elements having substantially similar lengths;
two tensioning elements extending through a center portion of the second section;
two spaced apart tensioning elements extending through the second section;
two elastic tensioning elements arranged generally parallel to each other;
two flexible tensioning elements arranged generally parallel to each other; and
two bendable tensioning elements arranged generally parallel to each other.

5. The splint of claim 1, wherein at least one of the first and second sections comprise engaging contact surfaces which are at least one of partially curved, generally asymmetrical, generally contoured, and generally structured and arranged to engage with one another.

6. The splint of claim 1, wherein the tension adjustment device is structured and arranged to adjust a tensile stress of the at least one tensioning element.

7. The splint of claim 1, wherein the tension adjustment device comprises:
an engaging section which is movably mounted to the at least one tensioning element;
an adjusting section which constitutes the portion of the tension adjustment device; and
an adjusting member which moves the engaging section away from the adjusting section.

8. The splint of claim 1, wherein:
the second section comprises a plurality of second sections arranged between the first section and the tension adjustment device;
each second section comprising two through openings; and the at least one flexible tensioning element comprises two flexible tensioning elements.

9. The splint of claim 1, wherein the splint is structured and arranged to bend when installed on a user and when the at least one tensioning element is tensioned.

10. A splint for an orthopedic joint bandage, comprising:
a first section;
a tension adjustment device;
a plurality of second section arranged between the first section and the tension adjustment device;
each second section comprising two through openings;
two tension members each having one end secured to the first section and another end secured to a portion of the tension adjustment device;
the two tension members being flexible and passing through the two through openings of each second section; and
each second section being movably mounted to the two tension members.

11. The splint of claim 10, wherein the tension adjustment device comprises:
an engaging section which is movably mounted to the two tension members;
an adjusting section which constitutes the portion of the tension adjustment device; and
an adjusting member rotatably mounted to the adjusting section and configured to move the engaging section away from the adjusting section.

12. The splint of claim 10, wherein the splint is structured and arranged to bend when installed on a user and when the at least one tensioning element is tensioned.

* * * * *